(12) United States Patent
Capri et al.

(10) Patent No.: US 12,070,353 B2
(45) Date of Patent: Aug. 27, 2024

(54) ULTRASONIC PERIODONTAL PROBE

(71) Applicants: TROPHY SAS, Marne la Vallee (FR); CARESTREAM DENTAL LLC, Atlanta, GA (US); UNIVERSITE DE TOURS, Tours (FR); INSTITUT NATIONAL DE LA SANTE ET DE LA RECHERCHE MEDICALE (INSERM), Paris (FR); CENTRE HOSPITALIER REGIONAL UNIVERSITAIRE DE TOURS, Tours (FR)

(72) Inventors: Arnaud Capri, Marne la Vallee (FR); David Roudergues, Marne la Vallee (FR); Jean-Marc Inglese, Bussy-Saint-Georges (FR); Herve Josso, Marne la Vallee (FR); Edward Shellard, Atlanta, GA (US); Stephanie Chevalliot, Marne le Vallee (FR); Jean-Marc Gregoire, Mettray (FR); Frederic Ossant, Tours (FR); Aline Banquart, Marne le Vallee (FR)

( * ) Notice: Subject to any disclaimer, the term of this patent is extended or adjusted under 35 U.S.C. 154(b) by 61 days.

(21) Appl. No.: 17/423,493

(22) PCT Filed: Jan. 16, 2020

(86) PCT No.: PCT/EP2020/051055
§ 371 (c)(1),
(2) Date: Jul. 16, 2021

(87) PCT Pub. No.: WO2020/148402
PCT Pub. Date: Jul. 23, 2020

(65) Prior Publication Data
US 2022/0087646 A1   Mar. 24, 2022

Related U.S. Application Data

(60) Provisional application No. 62/793,357, filed on Jan. 16, 2019.

(51) Int. Cl.
*A61B 8/12* (2006.01)
*A61B 8/00* (2006.01)
(Continued)

(52) U.S. Cl.
CPC .................. *A61B 8/12* (2013.01); *A61B 8/08* (2013.01); *A61B 8/0875* (2013.01); *A61B 8/14* (2013.01);
(Continued)

(58) Field of Classification Search
None
See application file for complete search history.

(56) References Cited

U.S. PATENT DOCUMENTS 10,799,210 B1 * 10/2020 Zhang .................. A61C 9/0086
2010/0227295 A1 * 9/2010 Maev .................. A61B 8/0875
433/215

(Continued)

FOREIGN PATENT DOCUMENTS

WO  WO-2018149948 A1 * 8/2018 ............. A61B 8/085

*Primary Examiner* — Joel Lamprecht
*Assistant Examiner* — Ashish S Jasani (57) ABSTRACT

At least one embodiment of an ultrasonic periodontal probe, the ultrasonic periodontal probe comprising a grip portion having a longitudinal axis, a support member comprising a part having a longitudinal axis different from the longitudinal axis of the grip portion, and an ultrasonic device fastened to the grip portion via the support member, wherein the ultrasonic device is configured for emitting ultrasound signals within at least two emitting cones and for receiving corresponding echoed ultrasound signals, the at least two emitting cones extending in opposite directions with regard to a plane comprising the longitudinal axis of the grip portion.

4 Claims, 7 Drawing Sheets

(51) Int. Cl.
  *A61B 8/08*   (2006.01)
  *A61B 8/14*   (2006.01)
  *A61C 19/04*  (2006.01)

(52) U.S. Cl.
  CPC ............ *A61B 8/4254* (2013.01); *A61B 8/429* (2013.01); *A61B 8/4455* (2013.01); *A61B 8/4466* (2013.01); *A61B 8/4477* (2013.01); *A61B 8/4494* (2013.01); *A61B 8/469* (2013.01); *A61B 8/5207* (2013.01); *A61B 8/54* (2013.01); *A61B 8/585* (2013.01); *A61C 19/043* (2013.01)

(56) References Cited

U.S. PATENT DOCUMENTS

| | | | |
|---|---|---|---|
| 2013/0060144 A1* | 3/2013 | Culjat | A61B 8/14 600/459 |
| 2016/0045184 A1* | 2/2016 | Courtney | A61B 8/4494 600/424 |
| 2017/0119505 A1* | 5/2017 | Mörmann | A61B 1/24 |
| 2020/0008775 A1* | 1/2020 | Erkamp | A61B 8/4263 |

\* cited by examiner

ULTRASONIC PERIODONTAL PROBE

FIELD OF THE INVENTION

The present invention relates to the technical field of ultrasonic probes and of ultrasonic dental probes for periodontal applications such as periodontal depth pocket measurement.

BACKGROUND OF THE INVENTION

Ultrasound imaging has been adapted for intraoral use in a number of implementations and has been found to have particular utility for tasks such as measurement of periodontal pocket depth. Conditions such as gingivitis, for example, can be detected by sensing the acoustic response of tissues.

Because of the non-emission of ionizing radiation, ultrasound imaging is inherently safer than ionizing methods and also allows the repeatability of the examination if needed. Ultrasound imaging can be used as a substitute for, or a complement to, various types of radiography (cone beam computed tomography or CBCT, panoramic x-ray, or intraoral x-ray imaging), magnetic resonance imaging (MRI), or nuclear medicine.

Ultrasound imaging may use high-frequency sound waves, typically between 1 to 100 MHz. High frequency waves being more attenuated than low frequency waves for a given distance, high frequency waves are suitable mainly for imaging superficial structures, e.g. for dermatology, or dental imaging. For example, high frequency soundwaves may preferably be between 20 to 50 MHz for periodontal pocket investigation. Conversely, low frequency waves are suitable for imaging the deepest structures of the body.

An ultrasound imaging apparatus generally comprises one or several transducers that acts as ultrasound beam emitters and/or ultrasound beam receivers to receive echoes from the emitted signals. In addition, the ultrasound imaging apparatus may comprise various processing and display components used for generating and presenting images from acquired signals. An ultrasound beam emitter generates an ultrasound signal from an electrical signal and conversely, an ultrasound receiver generates electrical pulses from a mechanical ultrasound signal.

Objects in the path of emitted ultrasound signals return a portion of the ultrasound energy back to the transducer which generates electrical signals indicative of the detected structures. The electrical signals generated from the received ultrasound signal can be delayed for selected times specific to each transducer, so that ultrasonic energy scattered from selected regions adds coherently, while ultrasonic energy from other regions has no perceptible impact. Further, the emission of ultrasound signals can be delayed in order to enable adaptive focusing. The electronic adaptive focusing makes it possible to increase the resolution depending on the depth of the imaged organ.

Array processing techniques used for generating and processing received signals in this way are termed "beamforming".

Particular challenges with intraoral ultrasound imaging relate to the design of a probe that can be used for imaging a full set of intraoral structures, i.e. for positioning an ultrasound fan beam along the vertical axis of each tooth of a mouth on both buccal and lingual faces, without the need for extensive modification, reconfiguration, or changing of probe tips or other components. Indeed, to be efficient, the ultrasound probe window must be facing the regions to be imaged. The acoustic paths between the transducer and the regions to be imaged are ensured via coupling materials such as water-based gel to provide acoustic paths with minimal attenuation.

Therefore, there is a need for improving apparatus for ultrasound imaging of teeth, gums, and other intraoral features.

SUMMARY OF THE INVENTION

The present invention has been devised to address one or more of the foregoing concerns.

In this context, there is provided an ultrasonic periodontal probe adapted for ultrasound imaging of teeth, gums, and other intraoral features.

According to an aspect of the invention, there is provided a rigid ultrasonic periodontal probe comprising a grip portion having a longitudinal axis, a support member comprising a part having a longitudinal axis different from the longitudinal axis of the grip portion, and an ultrasonic device fastened to the grip portion via the support member, wherein the ultrasonic device is configured for emitting ultrasound signals within at least two emitting cones and for receiving corresponding echoed ultrasound signals, the at least two emitting cones extending in opposite directions with regard to a plane comprising the longitudinal axis of the grip portion.

The probe according to the invention can be used for imaging a full set of intraoral structures, i.e. for positioning an ultrasound fan beam along the vertical axis of each tooth of a mouth on both buccal and lingual faces, without the need for extensive modification, reconfiguration, or changing of probe tips or other components.

According to some embodiments, the ultrasonic device is offset from the longitudinal axis of the grip portion. The distance between the ultrasonic device and the longitudinal axis of the grip portion may belong to the range of zero to five centimeters.

According to some embodiments, the support member comprises at least two parts, each of the at least two parts having a longitudinal axis different from the longitudinal axis of the grip portion. The distance between the ultrasonic device and the longitudinal axis of the grip portion may be zero.

According to some embodiments, an ultrasound signal is emitted within a single emitting cone of the at least two emitting cones at a time. This increases the quality of the received signals and reduces power consumption.

According to some embodiments, the ultrasonic device comprises at least two transducers or arrays of transducers, one of the at least two transducers or arrays of transducers being configured for emitting ultrasound signals within one of the at least two emitting cones and the other of the at least two transducers or arrays of transducers being configured for emitting ultrasound signals within the other of the at least two emitting cones.

According to some embodiments, the probe further comprises a moving element, the moving element being configured for enabling the ultrasonic device to emit ultrasound signals within at least each of the at least two emitting cones.

According to some embodiments, the moving element comprises a moving transducer or array of transducers and/or comprises a moving deflector for redirecting an ultrasound signal received from a transducer or array of transducers and for redirecting an ultrasound signal to the transducer or array of transducer.

According to some embodiments, the moving element moves in a cavity filled with a coupling material to provide acoustic paths with minimal attenuation.

According to some embodiments, the probe further comprises a selector for selecting one of the at least two emitting cones for emitting an ultrasound signal.

According to some embodiments, the probe further comprises detection means for detecting predetermined features of received ultrasound waves or for detecting a contact between the probe and an external element, the detection means controlling the selector. This simplifies the use of the probes according to such embodiments.

According to some embodiments, the probe further comprises an indicator, the indicator providing an item of information regarding a direction according to which ultrasound signals are emitted or will be emitted for generating images. This helps the practitioner for imaging intraoral structures.

According to some embodiments, the indicator comprises a plurality of light emitting devices, the probe further comprising a plurality of power sources converting ultrasound waves into electrical energy, the activation of light emitting devices of the plurality of light emitting devices being indicative of locations where ultrasound waves have been received by at least one power source of the plurality of power sources.

According to some embodiments, the support member for fastening the ultrasonic device to the grip portion is temporarily deformable for enabling the distance between the ultrasonic device and the longitudinal axis of the grip portion to be adjusted, the support member being rigid after adjustment.

According to some embodiments, the probe further comprises a communication interface for transmitting data representing ultrasound signals received by the ultrasonic device to a remote device.

According to some embodiments, the probe further comprises processing means for processing ultrasound signals received by the ultrasonic device.

According to some embodiments, the probe further comprises a motion sensor, an orientation sensor, and/or a position sensor for determining at least one of a position, an orientation, a speed, a motion direction, and an acceleration of the probe.

BRIEF DESCRIPTION OF THE DRAWINGS

Other features and advantages of the invention will become apparent from the following description of non-limiting exemplary embodiments, with reference to the appended drawings, in which.

DETAILED DESCRIPTION OF EMBODIMENTS
OF THE INVENTION

The following is a detailed description of particular embodiments of the invention, reference being made to the drawings in which the same reference numerals identify the same elements of structure in each of the Figures.

In the drawings and text that follow, like components are designated with like reference numerals, and similar descriptions concerning components and an arrangement or interaction of components already described are omitted. Where they are used, the terms "first", "second", and so on, do not necessarily denote any ordinal or priority relation, but may simply be used to more clearly distinguish one element from another, unless specified otherwise.

As used herein, the term "energizable" relates to a device or set of components that perform an indicated function upon receiving power and, optionally, upon receiving an enabling signal.

When referring to the shape of an apparatus, the term "rigid" should be understood as the substantially non-deformable nature of the apparatus, in normal use, which means that the relative position of main elements of the apparatus is substantially constant (i.e. there is no significant shape deformation during use). For example, the relative position of a grip portion, of a support member, and of an ultrasonic device of a rigid ultrasonic periodontal probe is substantially constant when the periodontal probe is used for imaging intraoral structures. This does not prevent the apparatus from being deformable during a configuration step, for example in a case in which two elements of the apparatus are fastened with a lockable hinge. In addition, this does not prevent the apparatus from comprising slightly deformable parts. For example, the grip portion of a rigid ultrasonic periodontal probe may comprise a deformable handgrip such as a handgrip comprising elastic foam.

In the context of the present disclosure, the terms "viewer", "operator", and "user" are considered to be equivalent and refer to the viewing practitioner, technician, or other person who acquires, views, and manipulates an ultrasound image, such as a dental image, on a display monitor. An "operator instruction," "user instruction," or "viewer instruction" is obtained from explicit commands entered by the viewer, such as by clicking a button on the ultrasound probe or system hardware or by using a computer mouse or by using a touch screen or a keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

The term "subject" refers to the tooth or other portion of a patient that is being imaged and, in optical terms, can be considered equivalent to the "object" of the corresponding imaging system.

Figure 1A:
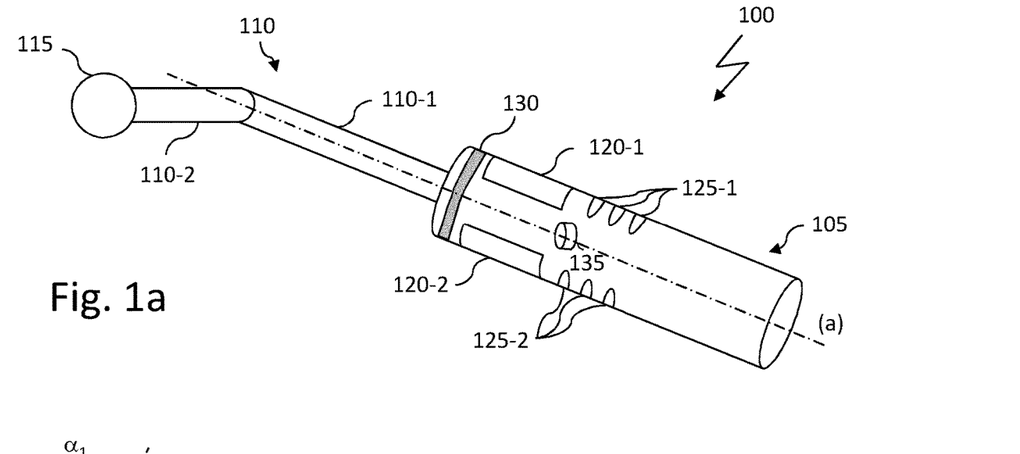
FIGS. 1a to 1d are schematic representations of a rigid ultrasonic periodontal probe according to some embodiments of the invention.
Figure 1B:
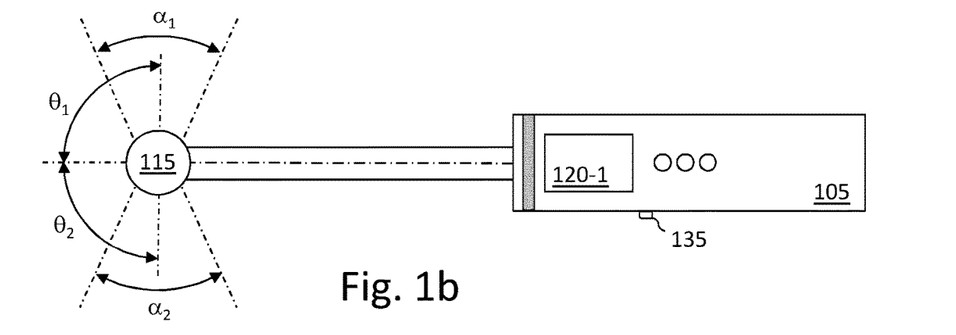
Figure 1C:
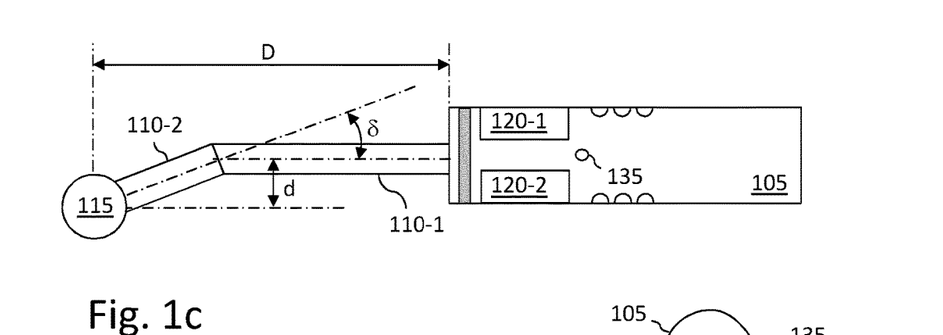
Figure 1D:
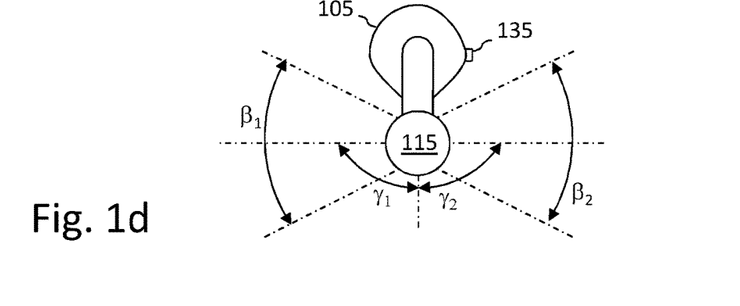

FIGS. 1a to 1d are schematic representations of a rigid ultrasonic periodontal probe according to some embodiments of the invention. FIG. 1a is a perspective view of the rigid ultrasonic periodontal probe while FIGS. 1b to 1d represent a top view, a side view, and a front view, respectively, of the same rigid ultrasonic periodontal probe.

The probe provides the ultrasound pulse signal emission and acquisition logic for generating an ultrasound beam and for beamforming functions. A computer (not represented) obtains acquired signal data corresponding to received pulse echoes, processed or not, and renders images of the examined objects on a display (not represented). The image content can also be stored for subsequent use or transmitted to another system or to a data storage apparatus or system.

As illustrated, the ultrasonic periodontal probe 100 comprises a grip portion 105, a support member 110, and an ultrasonic device 115 (also referred to as ultrasonic sensor). According to the illustrated example, support member 110 comprises two main parts denoted 110-1 and 110-2, the longitudinal axis of part 110-2 being different from the longitudinal axis of the grip portion 105. It is to be noted that according to other examples, part 110-2 is fastened directly to grip portion 105 (i.e. without using part 110-1). Therefore, according to the illustrated example, ultrasonic device 115 is rigidly fastened to grip portion 105 in such a way that it is offset from the grip portion with regard to its longitudinal axis. As apparent from FIG. 1c, ultrasonic device 115 is located at a distance d from the longitudinal axis (a) of grip portion 105. Distanced may be chosen between 0 and 5 centimeters. For the sake of illustration, it may be equal to 2 centimeters. Distance D between ultrasonic device 115 and grip portion 105 may be chosen between 4 and 25 centimeters. For the sake of illustration, it can be equal to 10 centimeters.

According to some embodiments, support member 110 may comprise two tubular members forming an angle δ between their longitudinal axis, may comprise one or more tubular members and a portion of an annular member, or may comprise any composition of members making it possible to axially offset the ultrasonic device from the grip portion.

As illustrated, grip portion 105 may comprise elements enabling a user to interface with functions of ultrasonic periodontal probe 100 and/or with a computer system processing signals acquired by ultrasonic periodontal probe 100. Such elements may comprise displays generically referenced 120 (e.g. standard displays or touch screens) and buttons generically referenced 125. According to some embodiments, all these elements or a subset of these elements are duplicated (120-1/120-2 and 125-1/125-2) so that a user may interact similarly with ultrasonic periodontal probe 100 and/or with a computer system processing signals acquired by ultrasonic periodontal probe 100 whatever the position of the ultrasonic periodontal probe between a first and a second position (the second position corresponding to a position that is in the opposite direction with regard to the first position, in a horizontal plane).

In addition, grip portion 105 may comprise a set of LEDs (acronym of light emitting devices), for example the ring of LEDs 130. As described hereafter, these LEDs may be indicative of measurement directions. Still additionally, grip portion 105 may comprise an encoding lug so that a user may identify a default position of ultrasonic periodontal probe 100. According to the illustrated example, the encoding lug is located on the left of the grip portion when the ultrasonic periodontal probe is in its default position (typically a position that has been defined during manufacturing and/or during a calibration phase, making it possible to correlate the position of the probe with the orientation of a displayed ultrasound image). In the given example, the default position is the position according to which the ultrasonic device is positioned in a vertical plane comprising the longitudinal axis of the grip portion, under the grip portion.

According to some embodiments, the LEDs or the ring of LEDs is arranged on the ultrasonic device or on the support member close to the ultrasonic sensor.

As illustrated in FIGS. 1b and 1d, ultrasonic device 115 may be configured to make measurements according to two opposite directions, with reference to a vertical plane that is perpendicular to a horizontal plane comprising the longitudinal axis (a) of grip portion 105. Ultrasound fan beams may belong to emitting cones having angular sectors $\alpha_1$ and $\alpha_2$ and angular sectors $\beta_1$ and $\beta_2$ that may be in a range of 20° to 160°.

The transducers of the ultrasonic periodontal probe may be of the A-mode, B-mode (or 2D mode), C-mode, M-mode, Doppler mode, Color Doppler mode, Continuous Doppler mode, Pulsed wave Doppler mode, Duplex mode, Pulse inversion mode, or Harmonic mode type, each of them being well-known to the one skilled in the art.

It is noted that although the directions of the two emitting cones (i.e. the cones in which ultrasound fan beams may be emitted) represented in FIGS. 1b and 1d are perpendicular to the longitudinal axis of grip portion 105 and to a vertical plane, these directions may be different. These directions may form angles $\theta_1$ and $\theta_2$ with regard to the longitudinal axis of grip portion 105 and angles $\gamma_1$ and $\gamma_2$ with regard to a vertical axis perpendicular to the longitudinal axis of grip portion 105, respectively, varying from about 20° to 160°, provided that these directions are opposite to each other, respectively, with regard to a plane comprising the longitudinal axis of grip portion 105, as illustrated in FIGS. 10a to 10d and 11a to 11c.

Still according to some embodiments, the probe tip comprising the ultrasonic device is removable so that it can be replaced and/or cleaned and disinfected. According to other embodiments, the probe tip is opened and protected with, for example, a rubber or a silicon member when used.

FIGS. 2a to 2d illustrate examples of use of an ultrasonic periodontal probe according to some embodiments of the invention.

Figure 2A:
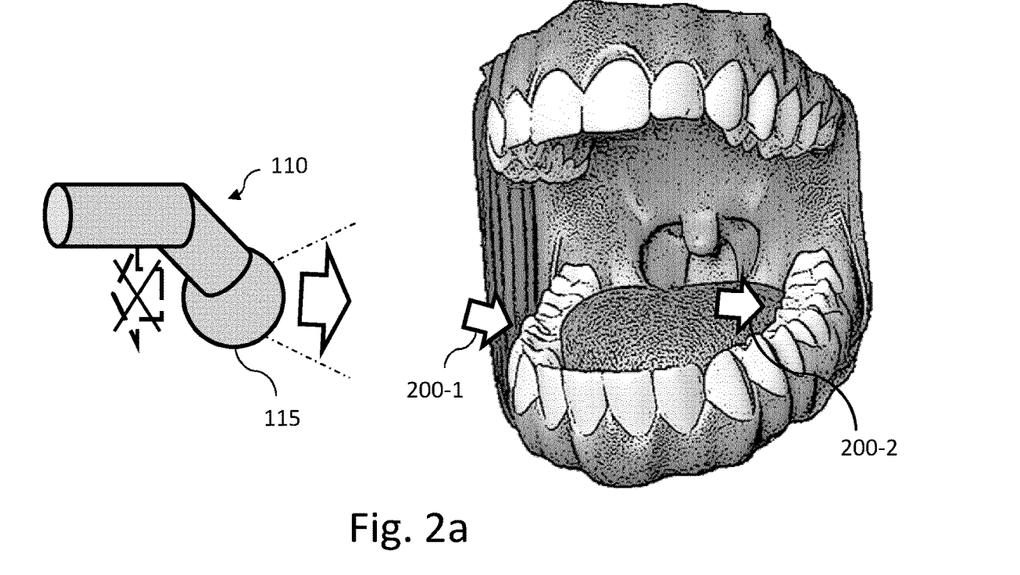
FIGS. 2a to 2d illustrate examples of use of an ultrasonic periodontal probe according to some embodiments of the invention.
Figure 2B:
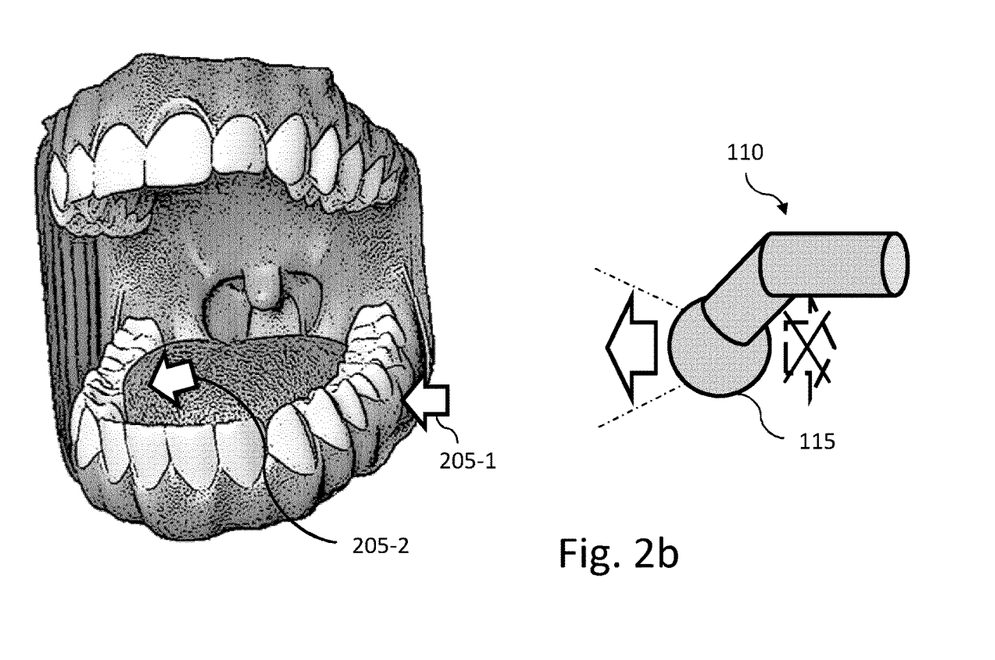
Figure 2C:
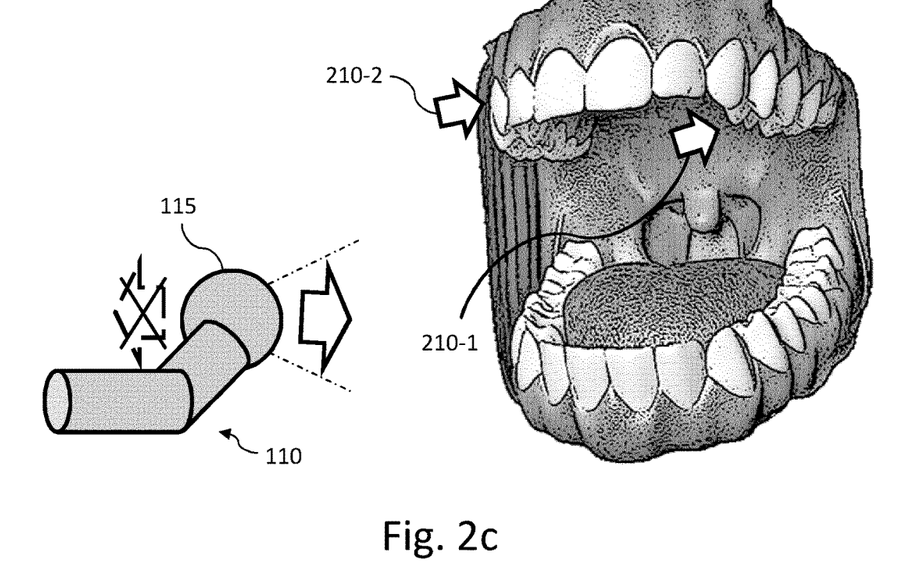
Figure 2D:
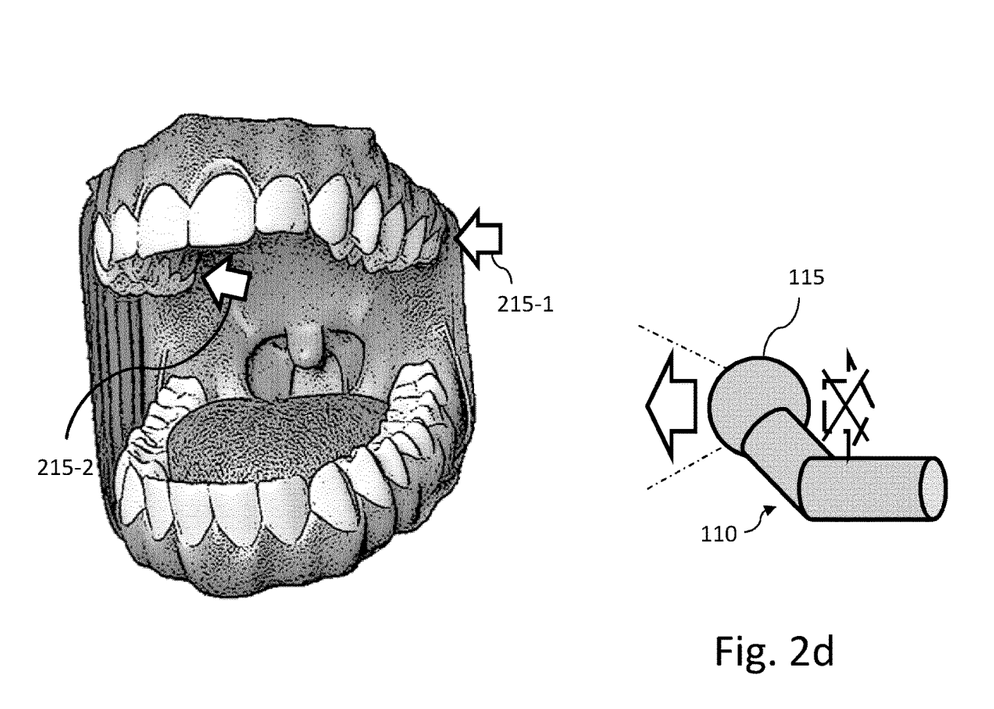

FIGS. 2a and 2b illustrate two examples of use of ultrasonic periodontal probe 100 in a position according to which ultrasonic device 115 is positioned under the grip portion (while considering the horizontal plane comprising the longitudinal axis of the grip portion), while FIGS. 2c and 2d illustrate two examples of use of ultrasonic periodontal probe 100 in a position according to which ultrasonic device 115 is above the grip portion (still considering the horizontal plane comprising the longitudinal axis of the grip portion).

As illustrated in FIGS. 2a and 2c, measurements are made only on the right side of ultrasonic device 115 from the perspective of the operator holding the probe. For these two measurements the same transducer may be used.

Conversely in FIGS. 2b and 2d, measurements are made only on the left side of the probe from the perspective of the operator holding the probe (indicated by arrow 115b). For these two measurements the same transducer may be used, which may be different from the one used for measurements of FIGS. 2a and 2c.

Accordingly, by choosing the appropriate orientation of ultrasonic periodontal probe 100 and by making measurements on the appropriate side of ultrasonic device 115, it is possible, using the same ultrasonic periodontal probe, to make a precise and full examination of the mouth of a patient. The side on which measurements are to be made may be selected by the user, for example using a manual selector (e.g. one of the buttons 125), or may be selected automatically using auto-detection. Auto-detection can be based on factors such as acoustic signal timing or on image features such as distribution of image values or image quality.

Therefore, ultrasonic periodontal probe 100 can be used to examine each portion of the jaw (enumerated examples hereinafter are from the perspective of the patient):
  left lingual of the mandible, reference 200-2 in FIG. 2a,
  right buccal of the mandible, reference 200-1 in FIG. 2a,
  left buccal of the mandible, reference 205-1 in FIG. 2b,
  right lingual of the mandible, reference 205-2 in FIG. 2b,
  left lingual of the maxilla, reference 210-1 in FIG. 2c,
  right buccal of the maxilla, reference 210-2 in FIG. 2c,
  left buccal of the maxilla, reference 215-1 in FIG. 2d, and
  right lingual of the maxilla, reference 215-2 in FIG. $2d_1$.

According to some embodiments, support member 110 can be deformed so as to make it possible to modify the distance between the ultrasonic device and the main axis of the grip portion, for example to adapt the ultrasonic periodontal probe to different types and/or sizes of mouths. This can result from using elastic materials and/or from using two or more sub-members that are fastened to each other using fastening means enabling changing the relative position of these sub-members. The fastening means advantageously comprise locking means to avoid modifying accidentally the relative position of the sub-members.

Figure 3A:
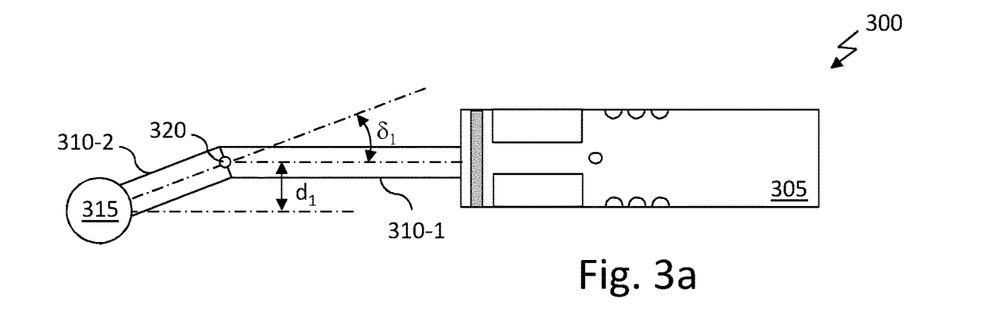
FIGS. 3a to 3c illustrate an example of a rigid ultrasonic periodontal probe having a configurable shape.
Figure 3B:
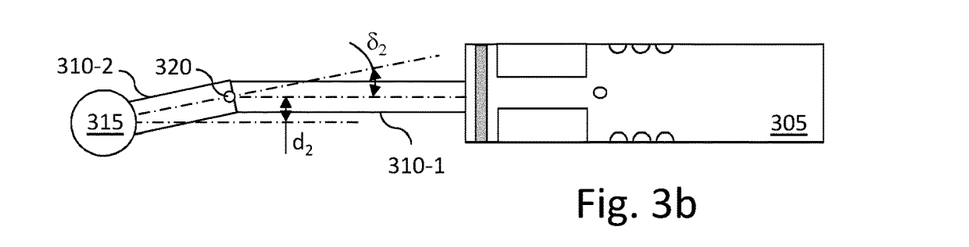
Figure 3C:
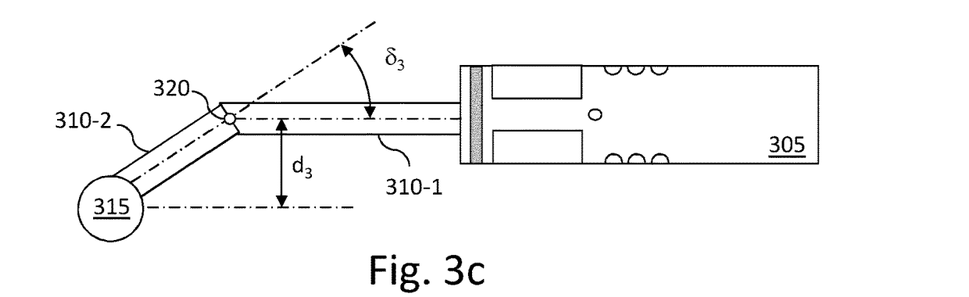

FIGS. 3a to 3c illustrate an example of a rigid ultrasonic periodontal probe having a configurable shape.

For the sake of illustration, ultrasonic periodontal probe 300 is similar to ultrasonic periodontal probe 100 described by reference to FIG. 1. However, the support member comprises two support sub-members denoted 310-1 and 310-2 fastened to each other with lockable hinge 320. Lockable hinge 320 makes it possible to modify the angle between support sub-members 310-1 and 310-2 in a first position of lockable hinge 320 (that is used temporarily for a setting purpose) and to rigidly fastened support sub-members 310-1 and 310-2 to each other in a second position of lockable hinge 320 (when the probe is used), resulting in a rigid ultrasonic periodontal probe having a configurable shape. As illustrated, the ultrasonic device denoted 315 is rigidly fastened to support sub-member 310-2 and sub-member 310-1 is rigidly fastened to grip portion 305. Therefore, by increasing or decreasing the angle between sub-members 310-1 and 310-2, the distance between ultrasonic device 315 and the longitudinal axis of grip portion 305 is increased or decreased accordingly, as illustrated with references $\delta_1$, $\delta_2$, and $\delta_3$ and $d_1$, $d_2$, and $d_3$, in FIGS. 3a to 3c.

In other embodiments, the ultrasonic periodontal probe may comprise a heat-deformable part such as but not limited to the support member to make it possible to adapt the shape of the support member and the relative position and/or orientation of the ultrasonic device in relation to the grip portion position, to the needs of the practitioner. Once the heat-deformable part is cold, the ultrasonic periodontal probe is rigid and can be used for imaging purposes.

Ultrasonic Periodontal Probe with Multiple Transducers or Arrays of Transducers

According to some embodiments, the ultrasonic periodontal probe comprises two or more transducers, or two or more arrays of transducers, arranged around an axis of the ultrasonic device that is parallel to the longitudinal axis of the grip portion, at least on each side of the ultrasonic device (when considering a measurement position of the probe). Still according to some embodiments, only a subset of the transducers or arrays of transducers are used to make measurements at a given time.

Figure 4:
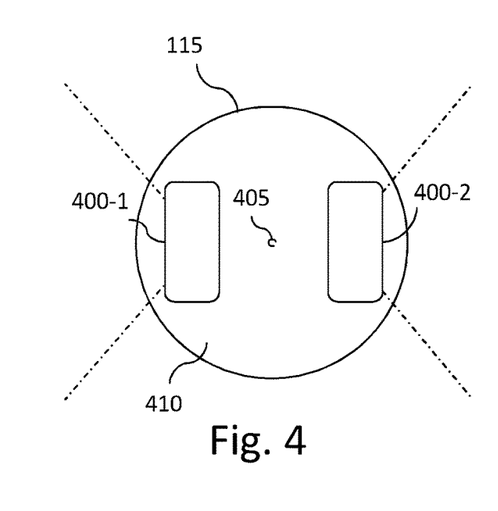
FIGS. 4 to 7 are sectional views of examples of an ultrasonic sensor of an ultrasonic periodontal probe according to some embodiments of the invention.

FIG. 4 is a sectional view of a first example of an ultrasonic device that comprises two transducers (or two arrays of transducers) arranged on each of its sides, rigidly fastened to the ultrasonic sensor. It is a sectional view according to a plane perpendicular to the longitudinal axis of the probe.

As illustrated, ultrasonic device 115 comprises two transducers (or arrays of transducers) 400-1 and 400-2, rigidly fastened to ultrasonic device 115, that are arranged on each side of the longitudinal axis 405 of the device (that is parallel to the longitudinal axis of the grip portion), with regard to a vertical plane. According to some embodiments, only one of the transducers (or arrays of transducers) is used to make measurements at a given time. This can be done by activating only one of them or by processing the signals received from only one of them. As described above, the transducer or array of transducers that should be used for making measurements can be selected by the user or can be selected automatically.

For the sake of illustration, the rigid ultrasonic periodontal probe may comprise a button, a switch, or a ring of buttons that may take, for example, the form of a rotatable sleeve or collar, for selecting the transducer or array of transducers that should be used. A touch-sensitive screen arranged on the ultrasonic periodontal probe may also be used to that end. The ultrasonic periodontal probe may also comprise a sensor for measuring mechanical pressure so that a transducer is selected automatically when the user presses the probe against the mandible or the maxilla.

According to some embodiments, an indication is displayed on a display or as a subset of one or more LEDs to provide an indication regarding which transducer is used.

Figure 5:
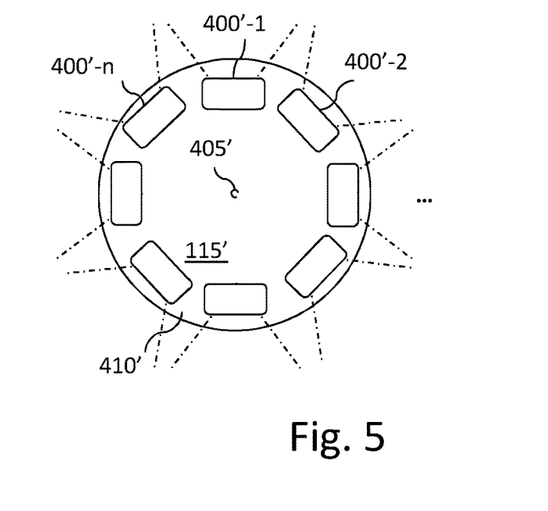

FIG. 5 is a sectional view of a second example of an ultrasonic device that comprises a ring of transducers (or of arrays of transducers). Again, it is a sectional view according to a plane perpendicular to the longitudinal axis of the probe.

As illustrated, ultrasonic device 115' comprises a ring of transducers (or of arrays of transducers) 400'-1 to 400'-n, rigidly fastened to ultrasonic device 115' that are arranged around the longitudinal axis 405' of the device (that is parallel to the longitudinal axis of the probe). According to some embodiments, one or several neighboring transducers (or arrays of transducers) are used to make measurements at a given time. Again, this can be done by activating only some of them or by processing the signals received from only some of them, the transducers (or arrays of transducers) to be used being selected by the user or automatically.

According to some embodiments, the ring of transducers comprises transducers for emitting ultrasound waves and transducers for receiving ultrasound waves that are different from the transducers for emitting ultrasound waves.

Still for the sake of illustration, the ultrasonic periodontal probe may comprise a button, a switch, or a ring of buttons that may take, for example, the form of a rotatable sleeve or collar, for selecting the transducer(s) or array(s) of transducers that should be used. A touch-sensitive screen arranged on the ultrasonic periodontal probe may also be used to that end. The ultrasonic periodontal probe may also comprise a sensor for measuring mechanical pressure so that transducer(s) or array(s) of transducers are selected automatically when the user presses the probe against the mandible or the maxilla.

According to some embodiments, an indication is displayed on a display or as a subset of one or more LEDs to provide an indication regarding which transducer(s) are used.

Ultrasonic Periodontal Probe with a 360° Transducer or Array of Transducers

Figure 6:
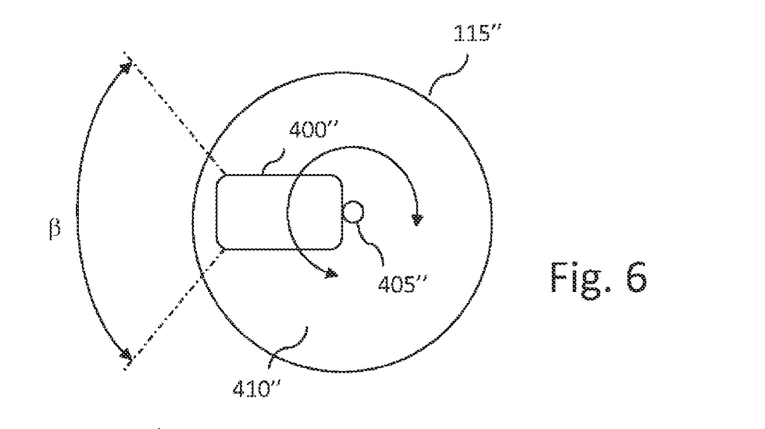

FIG. 6 is a sectional view of a third example of an ultrasonic device that comprises a single transducer (or array of transducers). Again, it is a sectional view according to a plane perpendicular to the longitudinal axis of the probe.

As illustrated, the single transducer (or array of transducers) 400" is rotatably mounted within cavity 410" of ultrasonic device 115" so that it can rotate around axis 405", that is parallel to the longitudinal axis of the grip portion. Therefore, the ultrasonic device can emit ultrasound signals according to a given lateral angular sector (denoted 13 in FIG. 6), that depends on the characteristics of the transducer (or array of transducers), and according to any angular position of the transducer (or array of transducers) over an angular sector that is greater than emitting angular sector 13, for example over a full 360° radius.

Ultrasound signals may be emitted according to given angular positions so as to make measurements only for angular sectors of interest. In such a case, the given angular positions may be defined by settings or by the user or may be dynamically adapted, for example as a result of an analysis of received ultrasound signals. For the sake of illustration, the ultrasonic periodontal probe may comprise a button, a switch, or a ring of buttons that may take, for example, the form of a rotatable sleeve or collar, for controlling the directions according to which measurements are to be made. A touch-sensitive screen arranged on the ultrasonic periodontal probe may also be used to select these directions. The ultrasonic periodontal probe may also comprise a sensor for measuring mechanical pressure so that the directions of measurements is set automatically when the user press the probe against the mandible or the maxilla.

According to some embodiments, an indication is displayed on a display or as a subset of one or more LEDs to provide an indication regarding the direction according to which measurements are made.

Alternatively, ultrasound signals may be emitted and measured from each of 360/β angular positions so that measurements are made for the full 360° radius. In such a case, only meaningful measured signals are preferably processed to render images.

Figure 7:
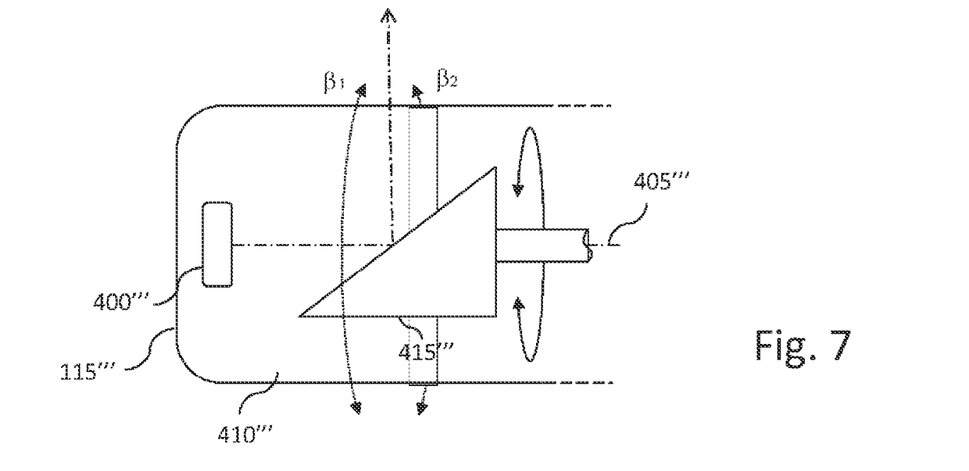

FIG. 7 is a sectional view of a fourth example of an ultrasonic device that comprises a single transducer (or array of transducers). It is a sectional view according to a vertical plane comprising or parallel to the longitudinal axis of the probe.

As illustrated, the single transducer (or array of transducers) 400''' is rigidly fastened within the ultrasonic device and a reflective element, or deflector, denoted 415 is rotatably mounted within cavity 410' of ultrasonic device 115''', in front of the transducer (or array of transducers) for enabling the latter to emit and/or receive ultrasound signals over a full 360° radius or over a portion of the full 360° radius.

According to the illustrated example, transducer (or array of transducers) 400''' is arranged so as to emit and receive ultrasound signals along a main direction given by axis 405''' that is parallel to the longitudinal axis of the probe. Reflective element 415''' is rotatably mounted in front of the transducer (or array of transducers) for redirecting emitted and/or received ultrasound signals according to lateral angular sectors.

Therefore, the ultrasonic device can emit ultrasound signals according to lateral angular sector $\beta_1$ or to lateral angular sector $\beta_2$, as illustrated, according to the characteristics of the transducer (or array of transducers) and of the reflective element, and according to any angular position of the reflective element over a full 360° radius.

As described by reference to FIG. 6, ultrasound signals may be emitted according to particular angular positions so as to make measurements only for angular sectors of interest. In such a case, the given angular positions may be defined by settings or by the user or may be dynamically adapted, for example as a result of an analysis of received ultrasound signals. Again, the ultrasonic periodontal probe may comprise a button or a switch, a ring of buttons that may take, for example, the form of a rotatable sleeve or collar, a touch-sensitive screen, or a mechanical pressure sensor for controlling the directions according to which measurements are to be made.

According to some embodiments, an indication is displayed on a display or as a subset of one or more LEDs to provide an indication regarding the direction according to which measurements are made.

Alternatively, ultrasound signals may be emitted and measured from each of the 360/β positions so that measurements are made for the full 360° radius. In such a case, only meaningful measured signals are preferably processed to render images.

According to some embodiments, cavity 410''' (where reflective element 415''' moves) is filled with coupling material such as water-based gel to provide acoustic paths with minimal attenuation.

A mechanism similar to the one described by reference to FIG. 6 may be used for enabling the reflective element to rotate in the ultrasonic device.

It is noted that the movable reflective element of FIG. 7 or the movable transducer(s) of FIG. 6 may move along any type of curves. The motion may be continuous or alternative (e.g. the movable reflective element or the movable transducer(s) go back and forth along a curve).

It is also noted that according to some embodiments, the reflective element and the transducer(s) are movable.

The transducer(s) in the several illustrated examples are mounted in a cavity (410, 410', 410" and 410'''). The external surface of each transducer is arranged at a distance of the internal surface of the cavity of the probe tip. In order to allow the propagation of soundwave from the transducer to the probe tip surface, the cavity is filled with coupling material such as water-based gel to provide acoustic paths with minimal attenuation. Several types of coupling material may be used, for example water (tap water or mineral water), humectant gel (such as the humectant gel known under the trademark Bioxtra, the Sensileave gel from Pierre Fabre, and the humectant gel from Sunstar).

According to some embodiments, the external surface of each transducer is arranged in contact with the internal surface of the cavity of the probe tip. In that case there is no need to fill the cavity with a coupling material.

It is noted here that there exist mechanisms for enabling a transducer or an array of transducers to rotate in an ultrasonic sensor, such as the one described in the document written by Xingying Wang et al., entitled "*Development of a Mechanical Scanning Device With High-Frequency Ultrasound Transducer for Ultrasonic Capsule Endoscopy*", IEEE Transactions on Medical Imaging, Vol. 36 No. 9, September 2017, pp. 1922-1929.

Electronic Elements of the Ultrasonic Periodontal Probe

Figure 8:
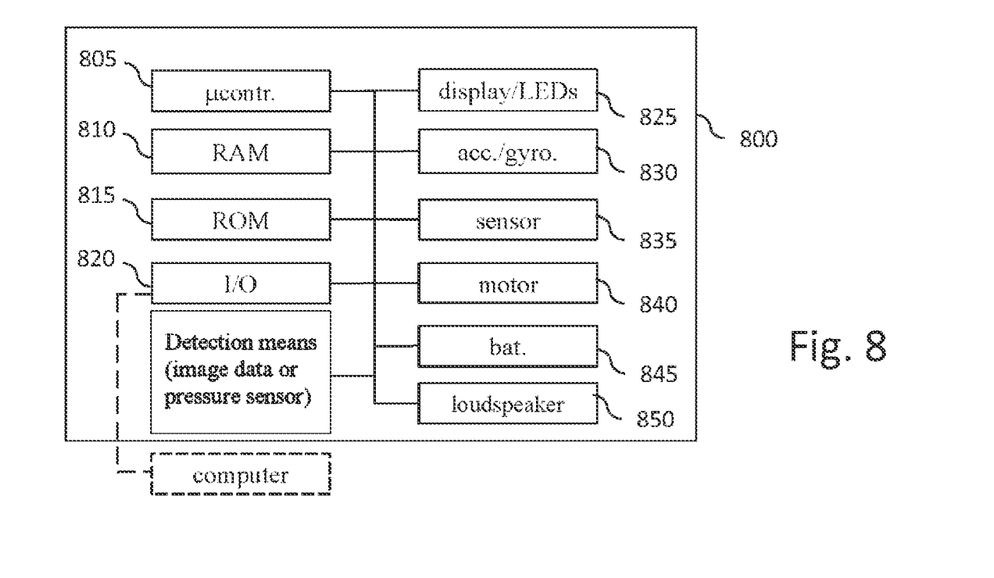
FIG. 8 is a schematic diagram illustrating an example of an electronic system of an ultrasonic periodontal probe according to some embodiments of the invention.

FIG. 8 is a schematic diagram illustrating an example of an electronic system of an ultrasonic periodontal probe according to some embodiments of the invention.

As illustrated, the electronic system 800 comprises buses and/or electrical connexions connecting:
- a microcontroller 805;
- a random access memory 810, denoted RAM, for storing the executable code for operating the ultrasonic periodontal probe as well as the registers adapted to record variables and parameters;
- a read-only memory 815, denoted ROM, for storing computer programs for operating the ultrasonic periodontal probe and/or configuration parameters;
- an input/output interface 820 to set the ultrasonic periodontal probe in signal communication with a remote computer, for interfacing the ultrasonic periodontal probe with the remote computer, for example to transmit measured signals and/or receiving commands for controlling some of the operations of the ultrasonic periodontal probe, the input/output interface being a wire or wireless interface, for example a wireless interface complying with the WiFi and/or Bluetooth standards (WiFi and Bluetooth are trademarks);
- a display and/or LEDs 825 for giving indication to the user, for example the state of the ultrasonic periodontal probe, a step or a next step to do, and/or the direction according to which measurements are made or will be made;
- a motion sensor, a position sensor, and/or an orientation sensor 830 comprising, for example, an accelerometer and a gyroscope, making it possible to determine the position, the orientation, the speed, and/or the acceleration of the ultrasonic periodontal probe, that may be used, for example, to identify commands by gesture type (e.g. a particular gesture may be used to select the directions according to which measurements are to be made);
- an ultrasonic device 835 comprising one or more transducers or arrays of transducers as described above;
- a motor 840 for moving parts of the ultrasonic sensor, for example a transducer, an array of transducers, or a reflecting element;
- a battery 845, rechargeable or not, for providing electrical power to the components of the electronic system; and
- a loudspeaker 850, for giving indications to the user, such as information relating to the state of the probe or performed measurements.

It is to be noted that the ultrasound periodontal device may comprise other electronic elements such that some of the electronic components mentioned above may not be required. For example, a motor is not required if the ultrasonic periodontal probe comprises several fixed transducers or arrays of transducers. Likewise, internal electrical power may not be required if the ultrasonic periodontal probe is connected to a remote computer via wires.

According to some embodiments, the executable code may be stored either in read-only memory 815 or on a removable digital medium such as for example a micro memory card. According to a variant, the executable code of the programs can be received from the remote computer via the input/output interface, in order to be stored in one of the storage means of the communication device 800.

Microcontroller 805 is adapted to control and direct the execution of the instructions or portions of software code of the program or programs for operating the ultrasonic periodontal probe according to some embodiments of the invention, the instructions being stored in one of the aforementioned storage means. After powering on, microcontroller 805 is capable of executing instructions from main RAM memory 810 relating to a software application after those instructions have been loaded from ROM 815 or from a remote computer for example.

Microcontroller 805, RAM 810, and/or ROM 815 may be implemented in hardware by a machine or a dedicated component, such as an FPGA (Field-Programmable Gate Array) or an ASIC (Application-Specific Integrated Circuit).

Upon reception, the acquired ultrasound signals may be processed, for example filtered, by electronic system 800, for example by microcontroller 805, before being transmitted to the remote computer through input/output interface 820. According to particular embodiments, the acquired ultrasound signals may be processed to generate images that are transmitted to the remote computer. Alternatively, the acquired ultrasound signals may be transmitted directly to the remote computer as raw data. The processing power and capabilities of electronic system 800 may depend on the processing to be applied to the acquired ultrasound signals.

The motion sensor and/or orientation sensor may be used to detect predetermined commands. For example, a movement of the ultrasonic periodontal probe to the right may indicate that measurements are to be made on the right side of the ultrasonic periodontal probe. Likewise, a movement of the ultrasonic periodontal probe to the left may indicate that measurements are to be made on the left side of the ultrasonic periodontal probe.

The motion sensor and/or orientation sensor may also be used to determine the position of the ultrasonic periodontal probe with regard to a default position. The determined position of the ultrasonic periodontal probe may be used to appropriately orient images generated from received ultrasound signals.

As described above, an indication may be displayed on a display or as a subset of one or more LEDs to provide an indication regarding the direction according to which measurements are made. According to some embodiments, ultrasound emitters and receivers are used to generate energy for energizing local indicators (for example small LEDs) in the vicinity of the probe tip.

To that end, piezoelectric elements, such as those used in transducers, having the capability to both generate a mechanical wave due to electrical excitation and, conversely, to generate an electrical pulse once placed under mechanical stress, are used. When using the ultrasonic periodontal probe, a transducer generates a number of ultrasound waves that are reflected and deviated by the observed tissues. During signal acquisition, for generating images, incident waves not only impact the transducer but also affect areas outside the transducer surface, including portions of the piezoelectric material not used for capturing signals, called piezoelectric wells for the sake of clarity. Therefore, it is possible to use part of the excess energy that is otherwise lost, in the vicinity of the emitters and receivers actually used to make measurements, by considering a number of piezoelectric sources for energy harvesting. These piezoelectric wells can capture excess energy that is not captured as part of the reflected acoustic signal and generate sufficient current to energize small LEDs and associated capacitive elements. As described above, the generated illumination from this energy harvesting can provide information to the user, to visually highlight the position or angular orientation of the emitted ultrasound beam. The generated illumination may even be strong enough to illuminate the scanned area.

According to some embodiments, the probe may be autonomous. In other words, the probe may be usable independently to any other systems, such as a remote computer. In this case, the probe may be configured to emit ultrasound signals, to acquire echoed ultrasound signals, to build an ultrasound image, to perform measurements and then to display notifications on the LCD display of the ultrasound probe. Consequently, the probe may comprise a microcontroller associated to memory (such as RAM and ROM) configured to process the acquired echoed ultrasound signals. Thus the microcontroller of the probe is configured to execute the instructions of the software application recorded in the embedded memory of the probe. Such a probe is then autonomous for the reconstruction of the ultrasound images, measurement of the echoed ultrasounds and notification of the measurements and/or the reconstruction to the operator.

Figure 9:
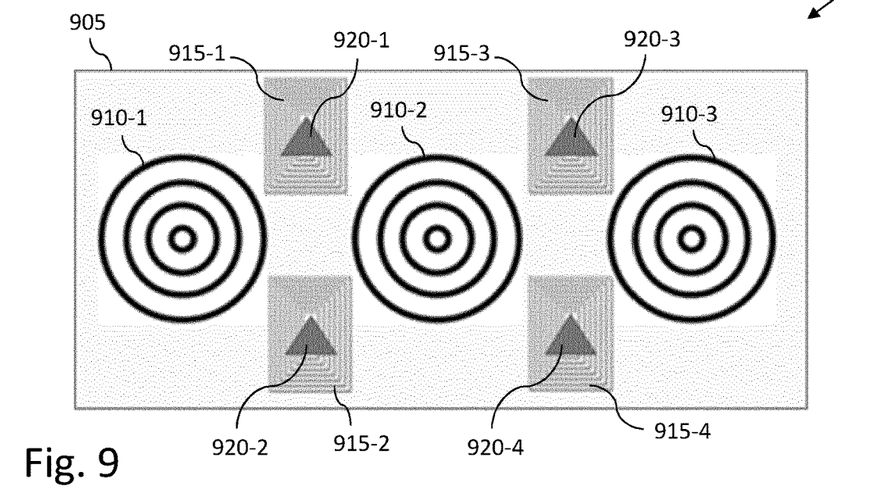
FIG. 9 illustrates an example of a portion of a transducer structure making it possible to emit and receive ultrasound signals and to energize LEDs when ultrasound signals are emitted and received.
Figure 10A:
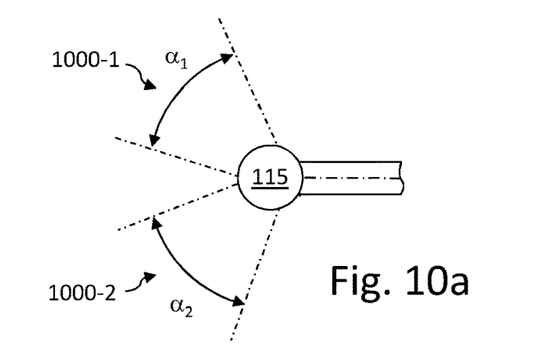
FIGS. 10a to 10d and 11a to 11c are schematic representations of emitting cones of an ultrasonic periodontal probe according to some embodiments of the invention, in which ultrasound fan beams may be emitted.
Figure 10B:
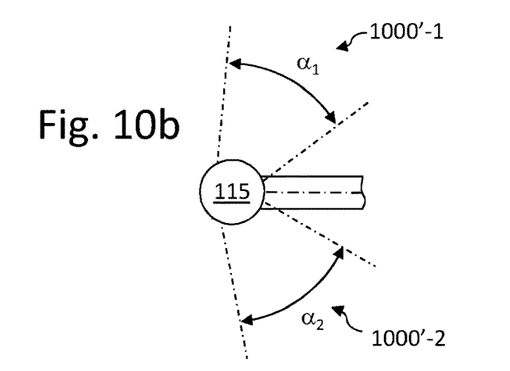
Figure 10C:
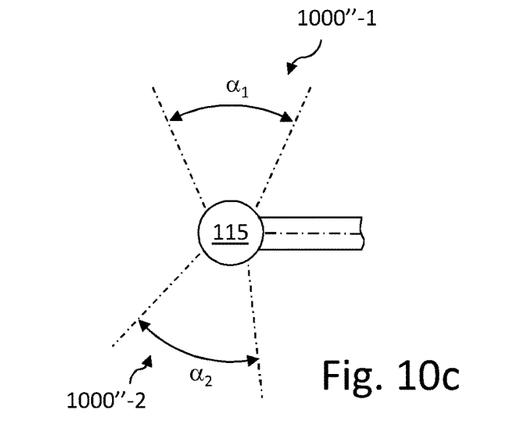
Figure 10D:
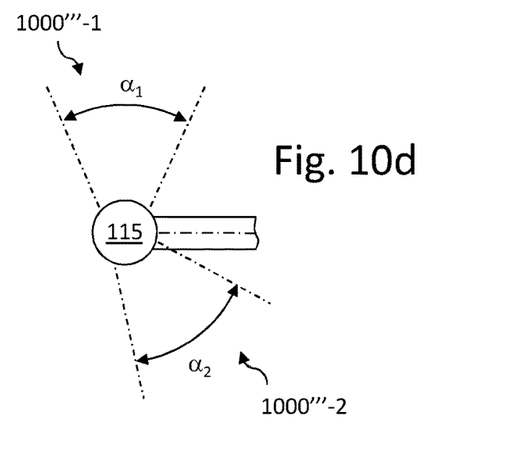

FIG. 9 illustrates an example of a portion of a transducer structure making it possible to emit and receive ultrasound signals and to energize LEDs when ultrasound signals are emitted and received.

As illustrated, transducer 900 comprises piezoelectric material 905 in which are formed emitters and receivers of ultrasound signals. Three emitters/receivers denoted 910-1 to 910-3 are represented in this example. As described above, portions of piezoelectric material 905 that are not used for emitting and receiving ultrasound signals with the aim of generating images are used to create piezoelectric energy harvesting area making it possible to energize associated LEDs. For example, piezoelectric energy harvesting areas 915-1 to 915-4 may be used to energize LEDs 920-1 to 920-4, respectively, upon reception of ultrasound waves, enabling a user to locate areas where ultrasound waves are received and thus, where measurements are made.

According to some embodiments, the ultrasonic periodontal probe comprises a light emitter configured to project a line of light, helping a user to position the ultrasonic periodontal probe appropriately. For the sake of illustration, the light emitter may be a laser source projecting a line on a tooth. The light line should be vertical when the ultrasonic periodontal probe is appropriately positioned enabling reliable measurements to be made.

Figures 11A, 11B:
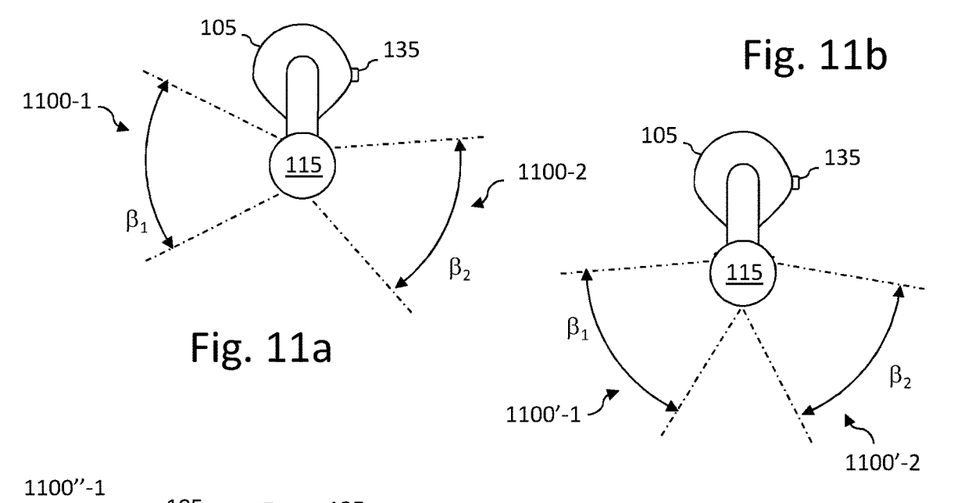
Figures 11C, 12, 13:
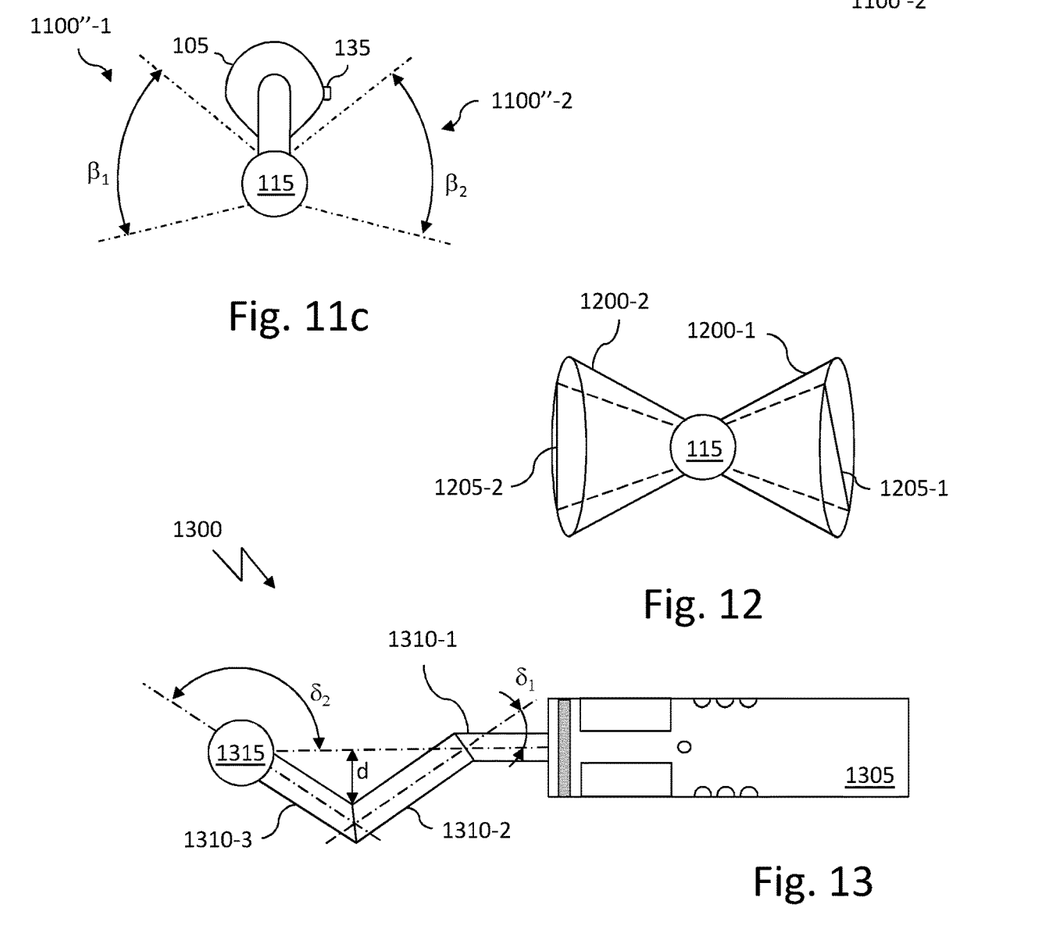
FIG. 12 illustrates ultrasound fan beams emitted in emitting cones of an ultrasonic periodontal probe according to some embodiments of the invention.
FIG. 13 is a schematic representation of an ultrasonic periodontal probe according to some embodiments of the invention.

FIGS. 10a to 10d and 11a to 11c are schematic representations of emitting cones of an ultrasonic periodontal probe according to some embodiments of the invention, in which ultrasound fan beams may be emitted. For the sake of illustration, FIGS. 10a to 10d are schematic representations of emitting cones in a plane that is perpendicular to the one in which emitting cones are represented in FIGS. 11a to 11c.

As illustrated, the main direction of emitting cones 1000-1, 1000'-1, 1000"-1, and 1000'"-1 is opposite to the main direction of emitting cones 1000-2, 1000'-2, 1000"-2, and 1000"'-2, respectively, with regards to plane comprising the longitudinal axis of the support member (a vertical plane according to the illustrated representations). In other terms, one emitting cone extends on one side of a plane comprising the longitudinal axis of the support member while the other emitting cone extends on the other side of the same plane.

Likewise, the main direction of emitting cones 1100-1, 1100'-1, and 1100"-1 is opposite to the main direction of emitting cones 1100-2, 1100'-2, and 1000"-2, respectively, with regards to plane comprising the longitudinal axis of the support member (a vertical plane according to the illustrated representation).

Still in other words, the main direction of an emitting cone belongs to the range]0°; 180° [while the main direction of the other emitting cone belongs to the range 1180°; 360° [. Preferably, the main direction of an emitting cone belongs to the range]20°; 160° [while the main direction of the other emitting cone belongs to the range]200°; 340° [.

FIG. 12 illustrates ultrasound fan beams emitted in emitting cones of an ultrasonic periodontal probe according to some embodiments of the invention.

As illustrated, an ultrasound fan beam 1205-1 may be emitted from ultrasonic device 115 in emitting cone 1200-1. Ultrasound fan beam 1205-1 corresponds to a surface that belongs to a plane comprising the ultrasound source and that is bounded by emitting cone 1200-1 (which depends on characteristics of the ultrasound source).

Likewise, ultrasound fan beam 1205-2 may be emitted from ultrasonic device 115 in emitting cone 1200-2.

FIG. 13 is a schematic representation of an ultrasonic periodontal probe according to some embodiments of the invention. It is a side view of the rigid ultrasonic periodontal probe.

Like probe 100 in FIGS. 1a to 1d, probe 1300 comprises a grip portion 1305, a support member 1310, and an ultrasonic device 1315. According to the illustrated example, support member 1310 comprises three main parts denoted 1310-1, 1310-2, and 1310-3, the longitudinal axis of parts 1310-2 and 1310-3 being different from the longitudinal axis of the grip portion 1305. According to the illustrated example, the angle of part 1310-2 and the angle of part 1310-3, with regards to the longitudinal axis of the grip portion 1305, denoted $\delta_1$ and $\delta_2$, respectively, are substantially supplementary angles. Therefore, if parts 1310-2 and 1310-3 are substantially of the same length, ultrasonic device 1315 is substantially aligned with grip portion 1305. However, the angle between parts 1310-2 and 1310-3, forming a concave support member, makes it possible to use efficiently probe 1300 for making measurements in the mouth of a patient.

According to some embodiments, the distance d from the longitudinal axis of grip portion 1305 and the farthest internal point of the support member is chosen between 0 and 5 centimeters. For the sake of illustration, it may be equal to 3 centimeters. The distance between ultrasonic device 1315 and grip portion 1305 may be chosen between 8 and 15 centimeters. For the sake of illustration, it can be equal to 10 centimeters.

It is to be noted that parts 1310-2 and 1310-3 may be replaced by a part having the shape of an arc of circle.

Methods and apparatus of the present invention can be applied while using any of the available ultrasound imaging modes. In addition, various types of beamforming algorithms can be implemented, depending on the type of exam and tissue being examined. Beamforming can be advantageous when the fan beam is directed along the long axis of the teeth.

While the invention has been illustrated and described in detail in the drawings and foregoing description, such illustration and description are to be considered illustrative or exemplary and not restrictive, the invention being not restricted to the disclosed embodiment. Other variations on the disclosed embodiment can be understood and performed by those skilled in the art, in carrying out the claimed invention, from a study of the drawings, the disclosure and the appended claims.

Such variations may derive, in particular, from combining embodiments as set forth in the summary of the invention and/or in the appended claims.

In the claims, the word "comprising" does not exclude other elements or steps, and the indefinite article "a" or "an" does not exclude a plurality. A single processor or other unit may fulfil the functions of several items recited in the claims. The mere fact that different features are recited in mutually different dependent claims does not indicate that a combination of these features cannot be advantageously used. Any reference signs in the claims should not be construed as limiting the scope of the invention.

The invention claimed is:

1. A rigid ultrasonic periodontal probe comprising:
    a grip portion having a longitudinal axis;
    a support member comprising a part having a longitudinal axis different from the longitudinal axis of the grip portion; and
    an ultrasonic device fastened to the grip portion via the support member,
    wherein the ultrasonic device is configured for emitting ultrasound signals within at least two emitting cones and for receiving corresponding echoed ultrasound signals, the at least two emitting cones extending in opposite and diverging directions with regard to a plane comprising the longitudinal axis of the grip portion, and the ultrasonic device comprises at least two transducers or arrays of transducers, one of the at least two transducers or arrays of transducers being configured for emitting ultrasound signals within one of the at least two emitting cones and the other of the at least two transducers or arrays of transducers being configured for emitting ultrasound signals within the other of the at least two emitting cones.

2. A rigid ultrasonic periodontal probe comprising:
    a grip portion having a longitudinal axis;
    a support member comprising a part having a longitudinal axis different from the longitudinal axis of the grip portion; and
    an ultrasonic device fastened to the grip portion via the support member,
    wherein the ultrasonic device is configured for emitting ultrasound signals within at least two emitting cones and for receiving corresponding echoed ultrasound signals, the at least two emitting cones extending in opposite directions with regard to a plane comprising the longitudinal axis of the grip portion, and
    wherein the probe further comprises a detection means for detecting predetermined features of received ultrasound waves or for detecting a contact between the probe and an external element, the detection means controlling a selector for selecting one of the at least two emitting cones for emitting an ultrasound signal.

3. A rigid ultrasonic periodontal probe comprising:
    a grip portion having a longitudinal axis;
    a support member comprising a part having a longitudinal axis different from the longitudinal axis of the grip portion;
    an ultrasonic device fastened to the grip portion via the support member, wherein the ultrasonic device is configured for emitting ultrasound signals within at least two emitting cones and for receiving corresponding echoed ultrasound signals, the at least two emitting cones extending in opposite directions with regard to a plane comprising the longitudinal axis of the grip portion; and
    the indicator providing an item of information regarding a direction according to which ultrasound signals are emitted or will be emitted for generating images.

4. The probe of claim 3, wherein the indicator comprises a plurality of light emitting devices and the probe further comprises a plurality of power sources converting ultrasound waves into electrical energy, the activation of light emitting devices of the plurality of light emitting devices being indicative of locations where ultrasound waves have been received by at least one power source of the plurality of power sources.

* * * * *